United States Patent
Harding et al.

(10) Patent No.: US 7,828,774 B2
(45) Date of Patent: Nov. 9, 2010

(54) SLEEVED CLIP SAFETY

(76) Inventors: Weston F. Harding, 2421 N. 910 West, Lehi, UT (US) 84043; Bart D. Peterson, 1988 W. Silver Spur Way, Farmington, UT (US) 84025

(*) Notice: Subject to any disclaimer, the term of this patent is extended or adjusted under 35 U.S.C. 154(b) by 171 days.

(21) Appl. No.: 12/119,332

(22) Filed: May 12, 2008

(65) Prior Publication Data
US 2009/0281499 A1 Nov. 12, 2009

(51) Int. Cl.
*A61M 5/178* (2006.01)

(52) U.S. Cl. .............. 604/164.08; 604/164.07; 604/164.09; 604/164.11; 604/263; 604/198

(58) Field of Classification Search ................ 604/164.01–164.11, 198, 263
See application file for complete search history.

(56) References Cited

U.S. PATENT DOCUMENTS

| | | | |
|---|---|---|---|
| 4,964,854 A | 10/1990 | Luther | |
| 5,215,528 A * | 6/1993 | Purdy et al. ............ | 604/164.08 |
| 5,409,461 A | 4/1995 | Steinman | |
| 5,558,651 A | 9/1996 | Crawford et al. | |
| 5,599,310 A | 2/1997 | Bogert | |
| 5,879,337 A | 3/1999 | Kuracina et al. | |
| 6,117,108 A | 9/2000 | Woehr et al. | |
| 6,221,047 B1 | 4/2001 | Greene et al. | |
| 6,224,569 B1 | 5/2001 | Brimhall | |
| 6,287,278 B1 | 9/2001 | Woehr et al. | |
| 6,322,537 B1 | 11/2001 | Chang | |
| 6,616,630 B1 | 9/2003 | Woehr et al. | |
| 6,652,486 B2 | 11/2003 | Bialecki et al. | |
| 6,692,471 B2 | 2/2004 | Boudreaux | |
| 7,264,613 B2 | 9/2007 | Woehr et al. | |
| 2002/0169418 A1 * | 11/2002 | Menzi et al. ........... | 604/164.07 |
| 2004/0092889 A1 | 5/2004 | Ferguson et al. | |
| 2004/0225260 A1 | 11/2004 | Villa et al. | |
| 2005/0027263 A1 | 2/2005 | Woehr et al. | |
| 2006/0270980 A1 | 11/2006 | Menzi et al. | |
| 2007/0038182 A1 | 2/2007 | Bialecki et al. | |
| 2007/0038186 A1 * | 2/2007 | Sutton et al. .......... | 604/164.08 |
| 2007/0112305 A1 | 5/2007 | Brimhall | |
| 2007/0179446 A1 | 8/2007 | Carrez et al. | |
| 2007/0179447 A1 | 8/2007 | Carrez et al. | |
| 2008/0249478 A1 * | 10/2008 | Ishikura et al. ........... | 604/198 |

FOREIGN PATENT DOCUMENTS

| | | |
|---|---|---|
| EP | 1911485 A1 | 4/2008 |
| EP | 1974765 A1 | 10/2008 |
| WO | 9305840 | 4/1993 |

* cited by examiner

*Primary Examiner*—Nicholas D Lucchesi
*Assistant Examiner*—Leah Stohr
(74) *Attorney, Agent, or Firm*—Craig Metcalf; Mony Ghose; Kirton & McConkie (57) ABSTRACT

The present invention relates to a safety clip device for shielding and retaining a tip of an introducer needle following insertion of a vascular catheter. The safety clip device includes a sleeve having an interlock system for locking together the sleeve and the catheter adapter. The sleeve houses a safety clip wherein a portion of the introducer needle extends through the safety clip and is pinched between arm portions of the safety clip. As the tip of the introducer needle is withdrawn from the catheter adapter, the tip of the introducer needle is retained in the safety clip, whereafter the safety clip is retained within the sleeve and the sleeve is released from the catheter adapter for safe disposal.

17 Claims, 10 Drawing Sheets

SLEEVED CLIP SAFETY

BACKGROUND OF THE INVENTION

This disclosure relates generally to vascular access devices and methods, including hypodermic needles, catheter assemblies, and devices used with catheter assemblies. Generally, vascular access devices are used for communicating fluid with the vascular system of patients. For example, catheters are used for infusing fluid, such as saline solution, various medicaments, and/or total parenteral nutrition, into a patient, withdrawing blood from a patient, and/or monitoring various parameters of the patient's vascular system.

Intravenous (IV) catheter assemblies are among the various types of vascular access devices. Over-the-needle peripheral IV catheters are a common IV catheter configuration. As its name implies, an over-the-needle catheter is mounted over an introducer needle having a sharp distal tip. The introducer needle is generally a hypodermic needle coupled to a needle assembly to help guide the needle and to facilitate its cooperation with the catheter. At least the inner surface of the distal portion of the catheter tightly engages the outer surface of the needle to prevent peelback of the catheter and thus facilitate insertion of the catheter into the blood vessel. The catheter and the introducer needle are assembled so that the distal tip of the introducer needle extends beyond the distal tip of the catheter with the bevel of the needle facing up away from the patient's skin. The catheter and introducer needle are generally inserted at a shallow angle through the patient's skin into a blood vessel.

In order to verify proper placement of the needle and/or catheter in the blood vessel, the clinician generally confirms that there is "flashback" of blood into a flashback chamber associated with a needle assembly. Flashback generally entails the appearance of a small amount of blood which is visible within the needle assembly. This allows a clinician to confirm placement of the catheter within a patient's blood vessel. Once proper placement of the distal tip of the catheter into the blood vessel is confirmed, the clinician may apply pressure to the blood vessel by pressing down on the patient's skin over the blood vessel distal of the introducer needle and the catheter. This finger pressure momentarily occludes the vessel, minimizing further blood flow through the introducer needle and the catheter.

The clinician may then withdraw the introducer needle from the catheter. The introducer needle may be withdrawn into a needle tip shield or needle shield that covers the needle tip and prevents accidental needle sticks. In general, a needle tip shield includes a housing, a sleeve, or other similar device that is designed such that when the needle is withdrawn from the patient, the needle tip will be trapped/captured within the needle tip shield. The purpose of the needle tip shield is to house the tip of the needle in a secure location, thereby reducing the possibility of needle sticks when the needle and needle tip shield are separated properly from the catheter. The catheter, conversely is left in place to provide intravenous access to the patient.

The separation of the needle assembly from the catheter portions of the catheter assembly presents numerous potential hazards to the clinicians and others in the area. As indicated above, there is a risk of accidental needle sticks if the needle tip is not secured properly in a needle tip shield. Additionally, because the needle has been in contact with blood in the patient's vasculature, blood is often present on the exterior of the needle and is often present inside the lumen of the needle. As the needle is withdrawn, there is a risk that this blood will drip from the needle tip or come into contact with other surfaces to expose clinicians and equipment to blood. Additionally, it has been observed that withdrawing a needle from a catheter assembly often imparts energy to the needle assembly, such as by the intentional or unintentional bending forces applied to the needle during removal. This energy has been observed to cause blood to splatter or spray from the needle as the needle wiggles and shakes with stored energy once it is free from the catheter assembly. While prior needle assemblies have provided needle tip shields to reduce the occurrence of needle sticks, these prior enclosures and clips have not sufficiently addressed the risk that clinicians and equipment may be exposed to blood from the needle without experiencing a needle stick. While the problem of blood exposure from needle tips used in over-the-needle catheters is a common problem, blood exposure risks are also problematic in other uses of hypodermic needles where the needle tip has been in contact with blood. The present disclosure presents systems and methods to significantly limit and/or prevent such blood exposure.

BRIEF SUMMARY OF THE INVENTION

The systems and methods of the present disclosure have been developed in response to problems and needs in the art that have not yet been finally resolved by currently available vascular access systems and methods. Thus, these systems and methods are developed to provide safer vascular access systems that reduce blood exposure.

A vascular access system may include a needle shielding system. The needle shielding system may include a needle, and in one embodiment, the needle shielding system includes a hypodermic needle. The needle is a tubular shaft with a needle tip on a distal end and an opening on a proximal end. The needle also includes a needle feature, such as a crimp or ferrule, at a location along the exterior of the needle and generally located near the distal end of the needle. The needle feature is attached to the needle in an irreversible manner such that the feature is unable to be removed from the needle. The needle feature is positioned along the exterior of the needle so as to interact with a safety clip as described below.

The needle shielding system may include a safety clip positioned around the needle. The safety clip includes a generally cylindrical base wherein a first side of the base is closed and a second side of the base is open. The first side of the base comprises a cannula port such that the needle may slidably extend through the cannula port and into the base of the safety clip. For example, in one embodiment the cannula port has an inner diameter is that is greater than the outer diameter of the needle shaft but is less than the outer diameter of the needle feature such that the needle may translate through the cannula port, but the needle feature may not translate through the cannula port.

The safety clip base further comprises at least one arm, wherein the arm extends distally from the base in an orientation parallel to the needle. The safety clip further comprises a flap that extends perpendicularly from the distal end of the arm such that the flap pinches the tubular shaft of the needle. This biases the arm and the flap of the base in a radially outward direction. The base of the safety clip further comprises at least one barb which extends radially outward from the base so as to interact with a complementary barb catch as located on the interior of a sleeve. The safety clip is positioned within a sleeve as described below.

The needle shielding system may also include a sleeve which is generally tubular and houses the safety clip. The sleeve includes a proximal and a distal opening. The safety clip is housed within the sleeve and the arm of the safety clip extends from the sleeve through the distal opening. Additionally, the proximal end of the needle shaft extends through the proximal opening. However, the proximal opening of the sleeve does not permit the base of the safety clip to exit the sleeve. For example, in one embodiment the proximal end opening of the sleeve has an inner diameter that is less than the outer diameter of the safety clip but that is greater than the outer diameter of the needle shaft. The outer diameter of the safety clip base is slightly less that the inner diameter of the sleeve such that the safety clip may translate within the sleeve in a slidable fashion. The sleeve may also include a complementary barb catch on the interior surface of the sleeve. As such, the barb of the safety clip base may interact with the barb catch of the sleeve in an irreversible manner such that the safety clip is locked within the interior of the sleeve. This process is described in detail below.

The sleeve may also include a hinged interlock flange wherein a section of the sleeve is cut such that a window is formed. The window may have three unattached sides and one hinged side such that the remaining hinged cut-out is an interlock flange. The interlock flange may hinge outwardly from the outer surface of the sleeve and interact with an interlock mate as located on the inner surface of a catheter adapter. The interlock flange may include an interlock finger for engaging an interlock mate and may also include a safety clip contact for maintaining contact with the at least one arm of the safety clip. For example, in one embodiment, the proximal end of the sleeve comprises a complementary barb catch located on the interior surface of the sleeve. The distal end of the sleeve is cut such that an interlock flange is hingedly attached to the sleeve. In this same embodiment, the cut in the sleeve results in a window being formed. The window is generally rectangular having three unattached sides and a fourth attached side comprising a hinge. The hinge attaches the interlock flange to the fourth side of the window. The interlock flange of this embodiment further comprises an interlock finger extending outwardly from the outer surface of the interlock flange. The interlock finger compatibly engages an interlock mate as formed on the inner surface of a catheter adapter. The interlock flange further comprises a safety clip contact that extends inwardly from the inner surface of the interlock flange and maintains contact with the arm of the safety clip. For example, in one embodiment the safety clip contact and the interlock finger are molded extensions of the interlock flange. The safety clip contact maintains contact with the outer surface of the at least one arm of the safety clip and the outwardly biased arm of the safety clip outwardly biases the interlock flange. As such, the interlock finger is securely locked within the interlock mate as formed on the interior surface of the catheter adapter. The engaged interlock finger and interlock mate provide support for the sleeve and the catheter adapter as described below.

The needle shielding system may also include a catheter adapter. The catheter adapter comprises an opening adapted to receive the sleeve such that the interlock finger of the interlock flange may compatibly engage an interlock mate as formed on the interior surface of the catheter adapter. The catheter adapter may also include a catheter. The catheter is attached to the distal end of the catheter adapter and configured such that the needle and the needle feature are positioned in the catheter. As such, the needle is positioned to aid in insertion of the catheter into a patient. The catheter adapter has an inner diameter that is slightly greater than the outer diameter of the sleeve. As such, the sleeve may be inserted into the catheter adapter in a compatible manner. For example, in one embodiment the sleeve is fitted into the catheter adapter. As inserted, the interlock finger of the interlock flange compatibly engages the interlock mate as formed on the interior surface of the catheter adapter. In this same embodiment, the needle is housed within the catheter such that the tip of the needle extends distally beyond the distal end of the catheter. In this embodiment, the sleeve and the catheter adapter are locked together and supported by the engaged interlock finger and interlock mate.

The needle shielding system is actuated following insertion of the catheter into a patient. The actuation occurs as the needle tip is withdrawn from the catheter in a proximal direction. As such, the needle and needle feature are removed from the catheter and into the lumen of the catheter adapter. As the needle tip is drawn into the interior of the catheter adapter, the needle tip translates proximally beyond the flap of the safety clip arm. At that point, the flap no longer pinches the shaft of the needle. At this point the arm of the safety clip collapses inwardly such that the flap is moved into a position generally perpendicular to the needle and distal to the location of the needle tip. At this point, the flap covers the needle tip, preventing the needle tip from exiting the safety clip beyond the flap. As the proximal end of the needle's shaft translates in a proximal direction, the needle is drawn further into the interior of the safety clip until the needle feature catches on the cannula port. At this time the needle and the safety clip are drawn together into the interior of the sleeve.

As the needle and the safety clip are drawn into the interior of the sleeve, the flap of the safety clip arm is drawn proximally past the safety clip contact. As such, the safety clip contact no longer contacts the at least one arm of the safety clip. At that point, the interlock flange relaxes inwardly, disengaging the interlock finger from the interlock mate. As the interlock finger disengages from the interlock mate, the barb of the safety clip base is simultaneously engaged by the complimentary barb mate. This irreversibly locks the safety clip within the sleeve. With the interlock finger disengaged from the interlock mate, the sleeve, and the enclosed needle and safety clip, are no longer supported by the catheter adapter and may be removed from the catheter adapter for safe disposal.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
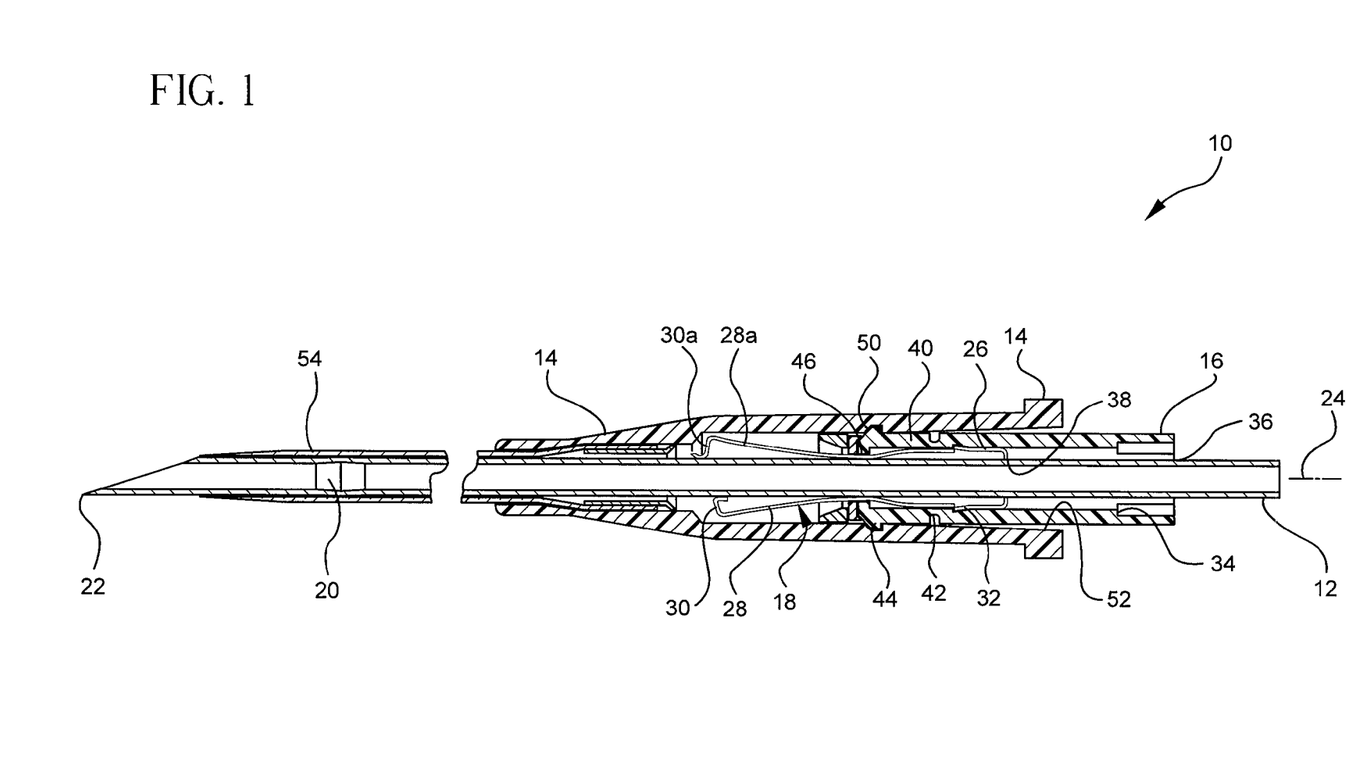
FIG. 1 is a cross-sectional view of a vascular access system, incorporating a safety clip, prior to insertion of the catheter into a patient.

Referring now to FIG. 1, a vascular access system 10 is illustrated comprising a needle 12, a catheter adapter 14, a sleeve 16 and a safety clip 18. The needle 12 may include a hypodermic needle having a tubular shaft or body and a needle feature 20 positioned towards the distal end of the needle 12. The needle feature 20 may include a ferrule or crimp designed to interact with safety clip 18 (discussed in detail below). In one specific embodiment the needle 12 is a hypodermic needle and the needle feature 20 is a ferrule. The needle feature 20 is positioned along the needle 12 such that the needle feature 20 and the needle tip 22 may be jointly retained within the safety clip 18 during removal of the needle 12 from the needle shielding assembly 10.

The needle 12 extends through the radial center of the needle shielding assembly 10 along a generally horizontal axis 24 and is directly housed within the safety clip 18. The safety clip 18 is positioned generally within the lumen of the sleeve 16 and comprises a base 26 and at least one arm 28. The arm 28 extends from the base 26 and is generally parallel to the needle 12. A flap 30 extends inwardly from the distal end of the arm 28 whereby the flap 30 maintains contact with the shaft of the needle 12. The flap 30 may comprise any design useful in interacting with and containing the needle tip 22. For example, in one embodiment the flap 30 is designed such that a terminal portion of the flap 30 curls towards the base 26 of the safety clip 18. In another embodiment, the safety clip base 26 comprises two arms 28 and 28a. Each arm 28 and 28a comprises a flap. A first flap 30 of the first arm 28 comprises an inwardly curled terminal end. A second flap 30a of the second arm 28a comprises an inward or outwardly curled terminal end. The first and second arm 28, 28a are configured such that the first arm 28 is shorter than the second arm 28a. As such, the second flap 30a may be positioned to overlap the first flap 30 when the needle tip 22 is withdrawn past the flaps 30 and 30a of the safety clip 18.

The base 26 of the safety clip 18 further comprises at least one barb 32. The barb 32 is positioned on the external surface of the base 26 and designed to compatibly engage a barb catch 34 as located on the interior surface of the sleeve 16 towards the proximal end of the sleeve 16. The base 26 of the safety clip 18 further comprises a cannula port 38 on the proximal end of the base 26. The cannula port 38 comprises an inner diameter that is slightly larger that the outer diameter of the needle 12 shaft such that the needle 12 may slidably translate through the cannula port 38. However, the inner diameter of the cannula port 38 is slightly smaller than the outer diameter of the needle feature 20 such that the needle feature 20 may not translate through the cannula port 38.

The safety clip 18 is partially housed within the lumen of the sleeve 16. For example, the base 26 is entirely housed within the sleeve 16, the arm 28 is partially housed within the sleeve 16, and the flap 30 is entirely not housed within the sleeve 16. The sleeve 16 is generally tubular and comprises a lumen wherein the safety clip 18 is partially housed. The sleeve 16 has an outer diameter that is selected to be slightly less than the inner diameter 32 of the catheter adapter 14. As such, the sleeve 16 may be inserted into the lumen of the catheter adapter 14. The sleeve 16 further comprises a first end and a second end, the first end having a cannula port 36. The cannula port 36 comprises an inner diameter that is slightly greater than the outer diameter of the needle 12 shaft. As such, the needle 12 may slidably translate through the cannula port 36. However, the inner diameter of the cannula port 36 is smaller than the outer diameter of the safety clip base 26. Thus, the base 26 of the safety clip 18 may not translate through the cannula port 36, but rather is retained within the sleeve 16. The second end of the sleeve 16 is generally open such that the needle 12 and the at least one arm 28 of the safety clip 18 extend beyond the second end of the sleeve 16 and into the lumen of the catheter adapter 14.

The sleeve 16 further comprises a barb catch 34 located on the interior surface of the sleeve 16 near the first end of the sleeve 16. The barb catch 34 comprises a recessed channel of a width and depth designed to compatibly receive the barb 32 of the safety clip. The base 26 of the safety clip 18 is configured to minimize the tolerance between the barb 32 and the inner surface of the sleeve 16 such that the inner surface of the sleeve 16 inwardly biases the barb 32. As the base 26 of the safety clip 26 is drawn towards the first end of the sleeve 16, the barb 32 is drawn into the barb catch 34. At this point, the inward bias of the barb 32 is released such that the barb 32 relaxes outwardly and engages the barb catch 34. Once engaged, the one-way compatibility of the barb 32 and the barb catch 34 prevent the safety clip 18 from exiting the opening of the second end of the sleeve 16.

The sleeve 16 further comprises an interlock flange 40 hingedly attached to the sleeve 16, as an appendage of the sleeve 16. In one embodiment, the interlock flange 40 comprises a section of the sleeve 16 that has been completely freed on three sides such that the interlock flange 40 forms a hinged window of the sleeve 16. The interlock flange 40 may be any length and therefore any portion of the sleeve 16 necessary to perform the function of interlocking the sleeve 16 and the catheter adapter 14.

The interlock flange 40 includes a hinge 42 formed by removing a portion of the sleeve's 16 exterior material such that a recess is formed between the sleeve 16 and the interlock flange 40. The hinge 42 is formed on the outer surface of the sleeve such that the interlock flange 40 may be outwardly biased with regard to the generally horizontal axis 24. The interlock flange 40 further comprises an interlock finger 44 located at the non-hinged end of the interlock flange 40 positioned on the outer surface of the interlock flange 40. The interlock finger 44 comprises a generally ramped shape and is configured to compatibly engage an interlock mate 50 as formed on the inner surface 52 of the catheter adapter 14. The interlock finger 44 extends radially outward from the outer surface of the interlock flange 40 and, therefore, also extends outwardly beyond the outer surface of the sleeve 16.

Finally, the interlock flange 40 comprises a safety clip contact 46 located at the non-hinged end of the interlock flange 40. The safety clip contact 46 is positioned on the inner surface of the interlock flange 40 so as to be opposite the interlock finger 44. The safety clip contact 46 comprises an inward extension of the interlock flange 40 which maintains contact with the arm 28a of the safety clip 18 in a pinching manner. Thus, the interlock flange 40 is outwardly biased by the pinching arm 28a of the safety clip 18. The outward bias of the interlock flange 40 secures the interlock finger 44 within the interlock mate 50 such that the sleeve 16 and the catheter adapter 14 are interlocked.

The catheter adapter 14 is generally tubular with an opening at the first end, the first end being adapted to support the sleeve 16 such that the inner diameter of the first end of the catheter adapter 14 is slightly greater than the outer diameter of the sleeve 16. The catheter adapter further comprises a second which forms a catheter 54. The catheter 54 comprises a flexible tube with a first end and a second end, the first end being housed within the opening of the second end of the catheter adapter 14. The first end of the catheter 54 has an opening adapted to receive the needle 12 and the needle feature 20. The first end of the catheter 54 is secured within the opening of the second end of the catheter adapter 14 in a fluid tight manner. The second end of the catheter 54 has an opening adapted to permit the needle tip 22 to extend beyond the catheter 54. The outer surface of the catheter's 54 second end is tapered towards the needle tip 22 so as to facilitate insertion of the catheter 54 into a patient.

In one embodiment, the second end of the sleeve 16 is housed within the catheter adapter 14. The sleeve 16 is locked within the catheter adapter 14 via an engagement of the interlock mate 50 by the interlock finger 44 of the outwardly biased interlock flange 40. In this same embodiment, the interlock flange 40 is outwardly biased by the pinching interaction of the safety clip contact 46 and the safety clip arm 28a. The safety clip arm 28a is outwardly biased due to the pinching interaction of the flap 30a and the shaft of the needle 12.

Figure 2:
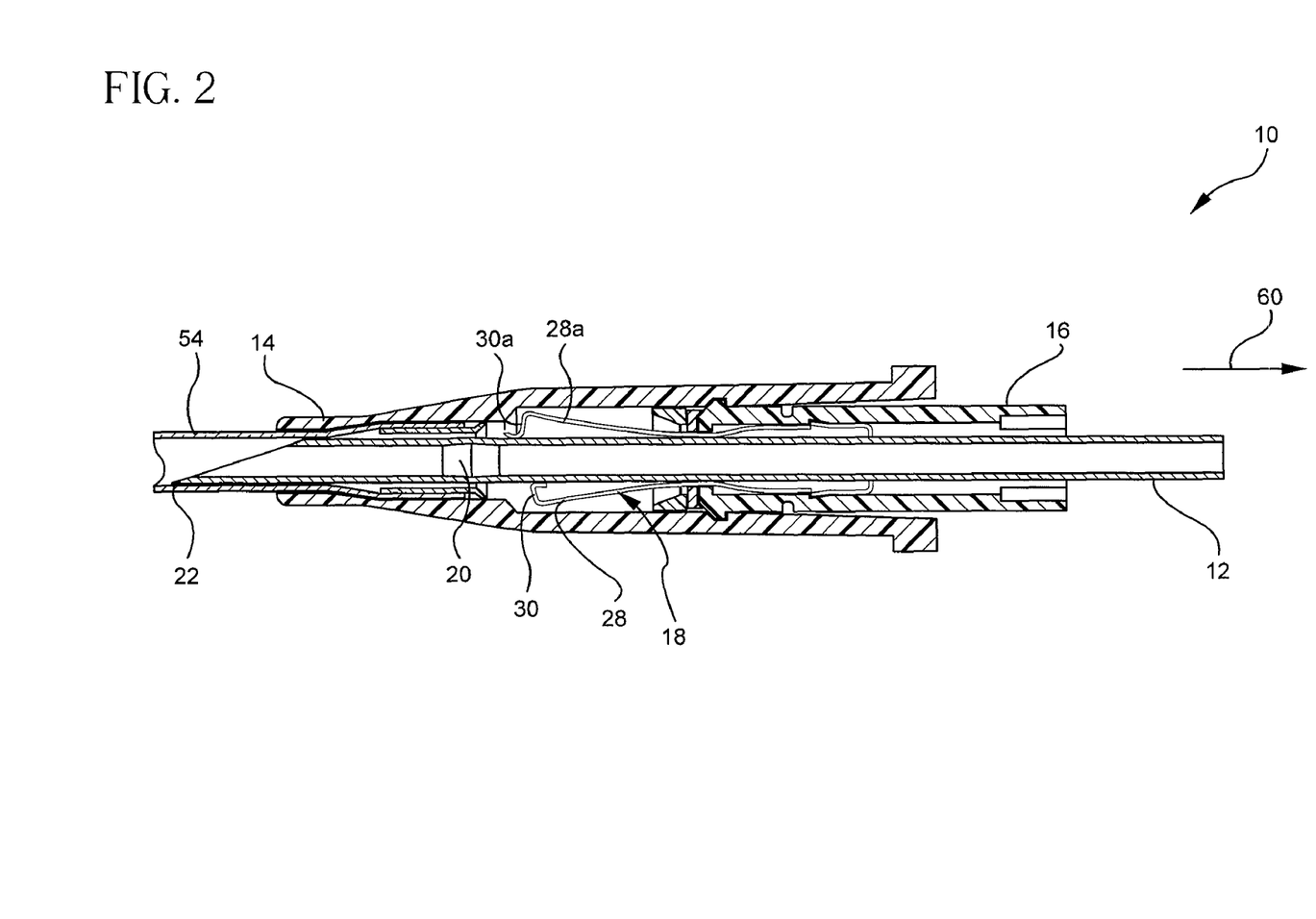
FIG. 2 is a cross section view of a vascular access system incorporating a safety clip following insertion of the catheter into a patient.
Figure 3:
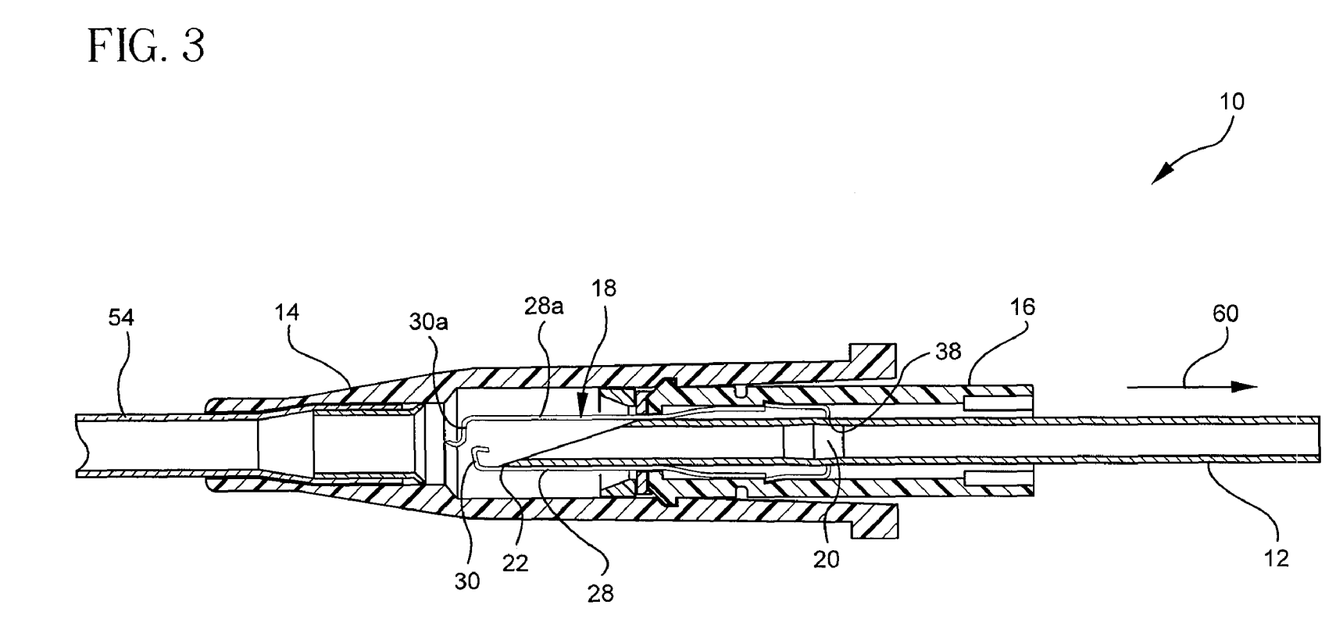
FIG. 3 is a cross-sectional view of a vascular access system having the needle tip withdrawn into the lumen of the safety clip.

Referring now to FIGS. 2-5, the needle shielding assembly 10 is illustrated following insertion of the catheter 54 into a patient (not shown) wherein the needle 12 is being removed from the catheter 54 in a proximal direction 60. Referring to FIG. 2, as the needle 12 is removed in a proximal direction 60, the needle feature 20 passes under the first flap 30a and the second flap 30. At this point, the first arm 28a and the second arm 28 are further biased outward to accommodate the passage of the needle feature 20. Referring to FIG. 3, as the needle 12 continues in the proximal direction 60, the needle tip 22 is drawn past the first flap 30a. At this point, the first flap 30a relaxes radially inward such that the first flap 30a no longer pinches the shaft of the needle 12. In this position, the first flap 30a acts as a blockade in preventing the needle tip 22 from advancing beyond the first flap 30a in a direction opposite to the proximal direction 60. As the needle 12 is further drawn in the proximal direction 60, the needle tip 22 is drawn past the second flap 30. At this point, the second flap 30 relaxes radially inward such that the second flap 30 no longer pinches the shaft of the needle 12. In this position, the second flap 30 acts as a blockade in preventing the needle tip 22 form advancing beyond the second flap 30 in a direction opposite to the proximal direction 60.

At this point, the needle 12 and needle feature 20 are entirely within the lumen of the safety clip 18. As such, the needle feature 20 is positioned against the cannula port 38 of the safety clip 18. In this position, the needle feature 20 is prevented from translating in a proximal direction 60 beyond the cannula port 38 due to the diameter of the cannula port 38 being smaller than the outer diameter of the needle feature 20. Therefore, as the needle 12 is drawn in a proximal direction 60, the needle feature 20 binds on the cannula port 38 and the safety clip 18 translates with the needle 12 and needle feature 20 in a proximal direction 60.

Figure 4:
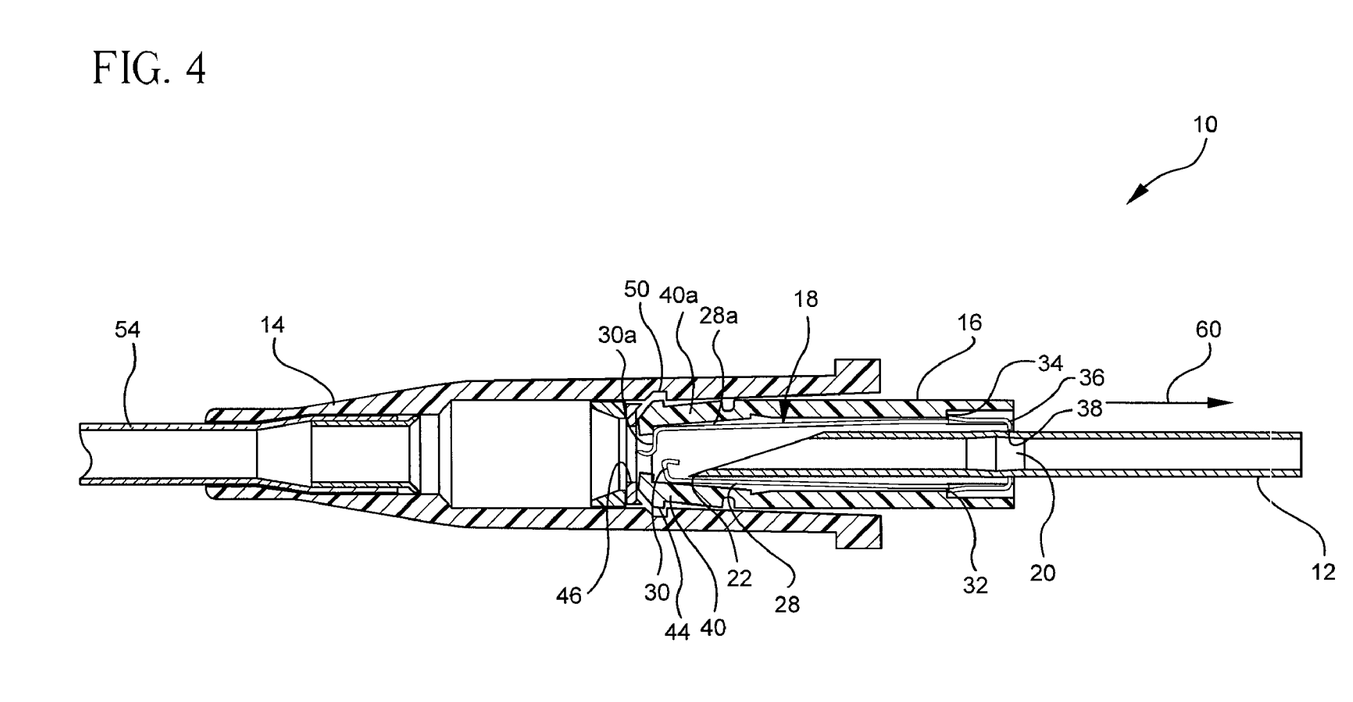
FIG. 4 is a cross-sectional view of a vascular access system having the safety clip withdrawn into the lumen of the sleeve.

Referring to FIG. 4, the safety clip 18 translates with the needle 12 in a proximal direction 60 until such time that the second flap 30 translates proximally beyond the first safety clip contact 46. At this point, the first safety clip contact 46 breaks contact with the first arm 28a and the first interlock flange 40 relaxes inwardly, disengaging the first interlock finger 44 from the respective interlock mate 50 of the catheter adapter 14. Upon further translation of the safety clip 18, the first flap 30a translates proximally beyond the second safety clip contact 46a. At this point, the second safety clip contact 46a breaks contact with the second arm 28 and the second interlock flange 40a relaxes inwardly, disengaging the second interlock finger 44a from the respective interlock mate 50 of the catheter adapter 14. At this point, the barb 32 engages the barb catch 34 in an irreversible manner such that the safety clip 18 is locked within the sleeve 16. Furthermore, in this locked position, the safety clip base 26 abuts the cannula port 36 of the sleeve 16. As such, the larger diameter safety clip base 26 is unable to translate beyond the smaller diameter cannula port 36 thereby preventing the safety clip 18 from further translation in a proximal direction 60.

Figure 5:
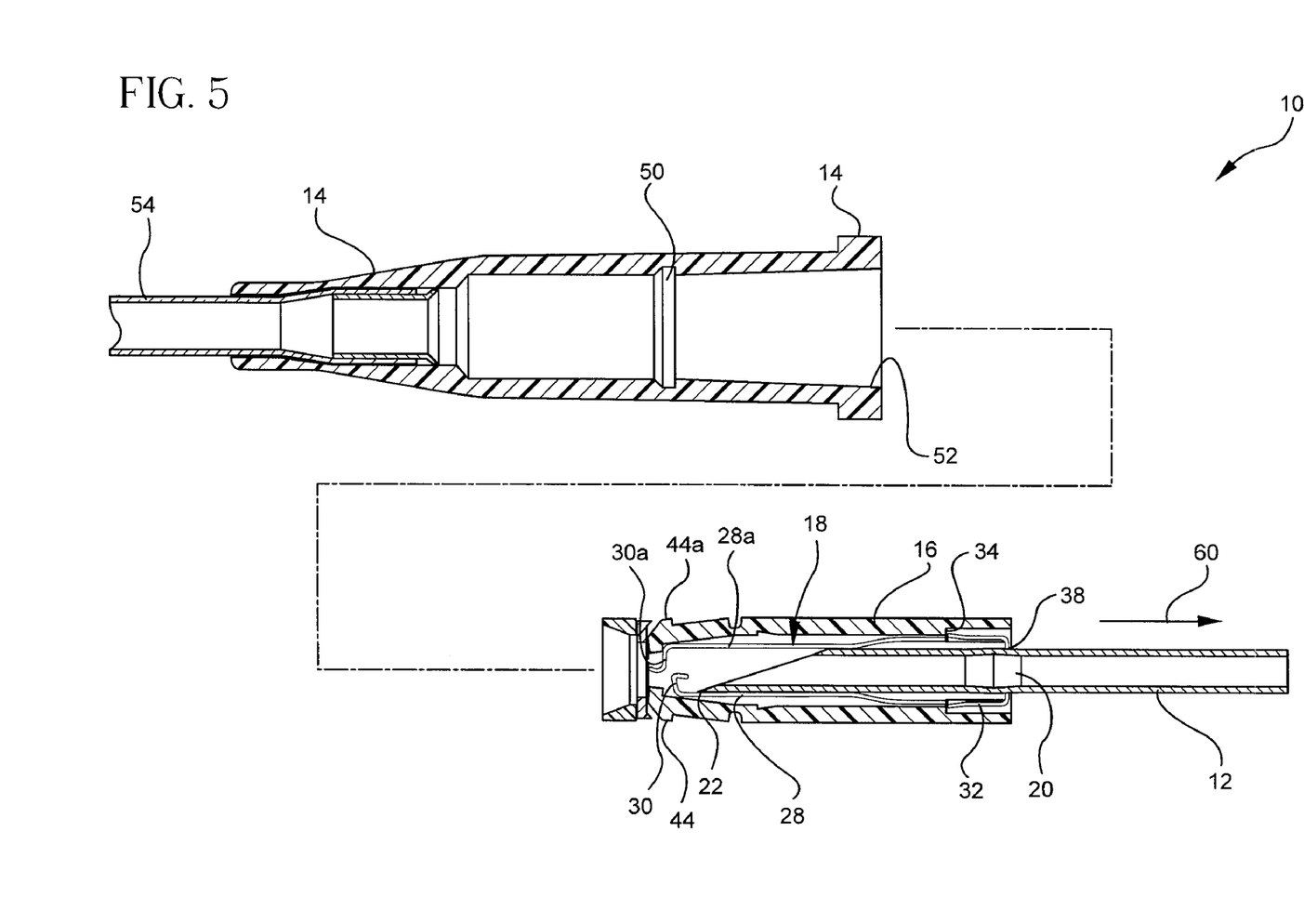
FIG. 5 is a cross section view of a vascular access system having the needle, safety clip, and sleeve members withdrawn from the catheter adapter.

Referring now to FIG. 5, the safety clip 18 is locked within the lumen of the sleeve 16, and the sleeve 16 is no longer interlocked with the catheter adapter 14. Thus, with both interlock fingers 44 and 44a disengaged from their respective interlock mates 50, additional translation of the needle in a proximal direction 60 withdraws the released sleeve 16 from the lumen of the catheter adapter 14. At this point, the needle tip 22 is safely locked within the safety clip 18 and the sleeve 16, and may be removed from the vascular access system 10 and disposed.

Figure 6:
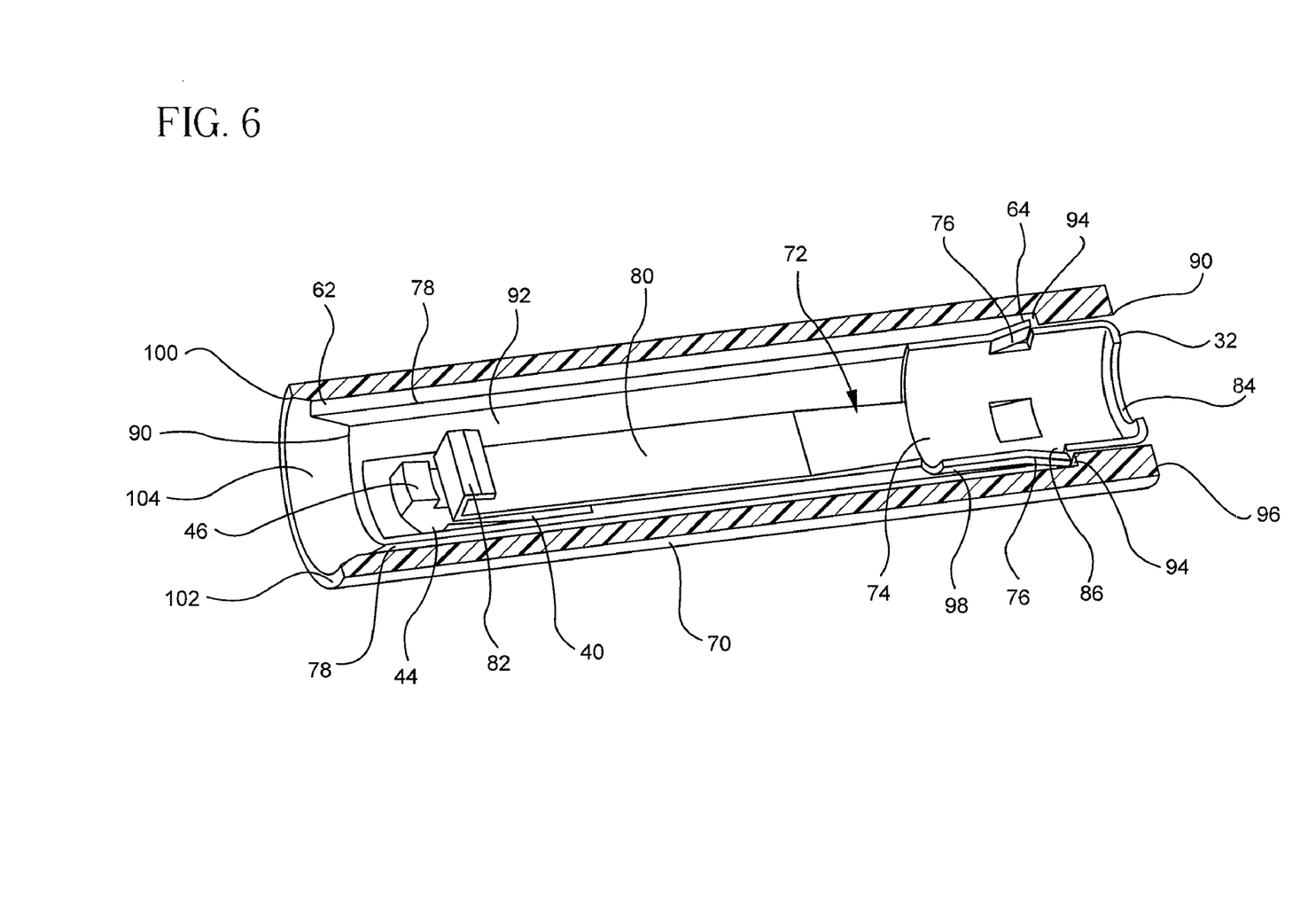
FIG. 6 is a cross-sectional view of a safety clip as housed within a sleeve.

Referring now to FIG. 6, an embodiment of the sleeve 70 and the safety clip 72 is illustrated. The base 74 of the safety clip 72 is modified to include a pair of alignment clips 76 to control alignment of the safety clip 72 within the sleeve 70. The safety clip 72 comprises a base 74, at least one arm 80, at least one flap 82, a cannula port 84, a barb 32 and a pair of alignment clips 76. The base 74 is generally tubular with a first end having a cannula port 84 and a second end being generally open. The base 74 further comprises at least one arm 80 extending laterally from the second end of the base 74. The arm 80 extends from the base in a generally horizontal axis 24 and terminates in a flap 82. The base 74 further includes a barb 32. The barb 32 comprises a partially cutout, flapped portion of the base 74 where three sides of the barb 32 are unattached to the base 74 and the fourth side is attached to the base 74. The barb 32 is outwardly biased such that the barb 32 opens towards the second end of the base 74. As such, the unattached end of the barb 32 may irreversibly engage the barb catch 34 of the sleeve 70.

Each alignment clip 76 comprises a partially cutout, flapped portion of the base 74. Each alignment clip 76 is outwardly biased such that the free end 86 of each alignment clips 76 opens towards the cannula port 84. The free end of each alignment clip 76 interacts with an alignment channel 78 of the sleeve 70 to prevent a rotation of the safety clip 72 with respect to the sleeve 70. As such, the alignment clip 72 ensures proper alignment of the barb 32 and the barb catch 34. Additionally, the alignment clip 72 ensures proper alignment of the arm 80 and the safety clip contact 46 of the sleeve 70.

The sleeve 70 is generally tubular with an opening on both a first end 96 and a second end 102. The sleeve 70 further comprises a first inner diameter 90 and a second inner diameter 100. The first inner diameter 90 approximates the outer diameter 98 of the safety clip base 74 such that the safety clip 72 is slidably housed within the sleeve 70. The sleeve 70 further includes a pair of alignment channels 78 comprising a recessed groove on the inner surface 92 of the sleeve 70. The alignment channels 78 are defined by a groove depth and groove width selected to accommodate translation of the alignment clips 76 through the alignment channels 78. The alignment channels 78 include a first end 62 and a second end 64, the first end 62 having an opening and the second end 64 having a clip catch 94. The clip catch 94 provides a closure of the alignment channel 78 such that the alignment channel 78 ends at a point prior to the first end 96 of the sleeve 70. The clip catch 94 interacts with the free end 86 of each alignment clip 76 to prevent the safety clip 72 from exiting the first end 96 of the sleeve 70. The position of the clip catch 94 is selected so as to coordinate the simultaneous interactions of the alignment clip 76 with the clip catch 94, and the barb 32 with the barb catch 34. Therefore, as the safety clip 72 is drawn towards the first end 96 of the sleeve 70, both interactions occur simultaneously and the safety clip 72 is locked in place within the sleeve 70.

The sleeve 70 further comprises a second inner diameter 100 located at the second end 102 of the sleeve 70. The second inner diameter 100 is greater than the first inner diameter 90 such that the inner surface 92 of the sleeve 70 is tapered from the first inner diameter 90 to the second inner diameter 100. The tapered portion of the inner surface 92 thereby provides clearance for the safety clip arm 80 to bias outwardly when the arm 80 and the flap 82 are positioned beyond the second end 102 of the sleeve 70. The sleeve further comprises a pair of interlock flanges 40. Each interlock flange 40 includes an interlock finger 44 and a safety clip contact 46 as described in the previous embodiment (see FIGS. 1-5 above).

Figure 7:
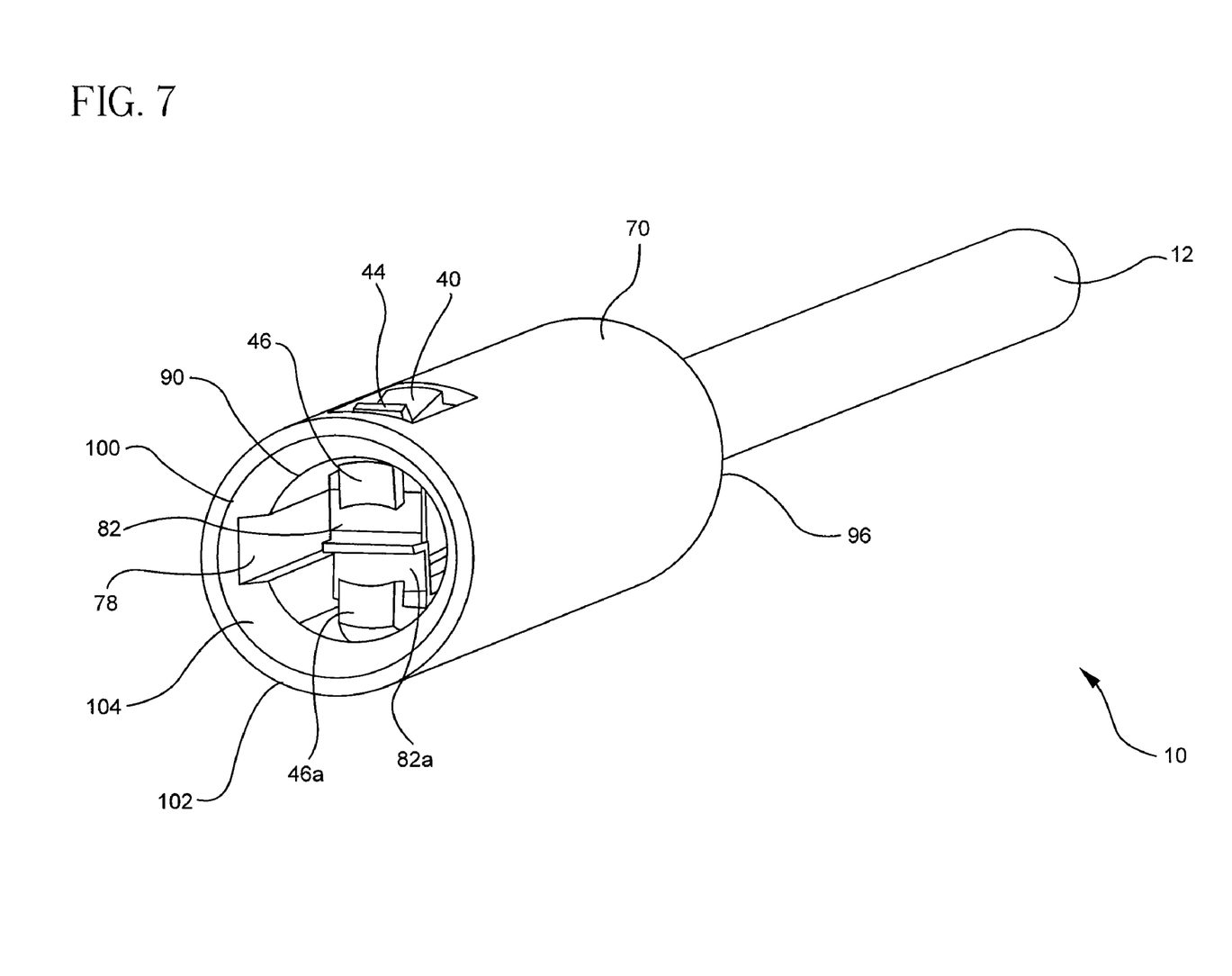
FIG. 7 is a perspective view of a sleeve retaining a needle and safety clip following removal of the sleeve from the catheter adapter.

Referring now to FIG. 7, the needle shielding assembly 10 is shown following removal of the sleeve 70 from the catheter adapter 14. As illustrated, the needle 12 and the safety clip flaps 82 and 82a have been retracted into the lumen of the sleeve 70. The first and second flaps 82 and 82a are in a closed position such that the needle tip 22 is enclosed within the safety clip. The interlock flanges 40 are relaxed inwardly such that the interlock fingers 44 have disengaged from the interlock mate of the catheter adapter 14. The safety clip contacts 46 and 46a are positioned in front of the safety clip flaps 82 and 82a thereby further securing the safety clip within the sleeve 70.

Figure 8:
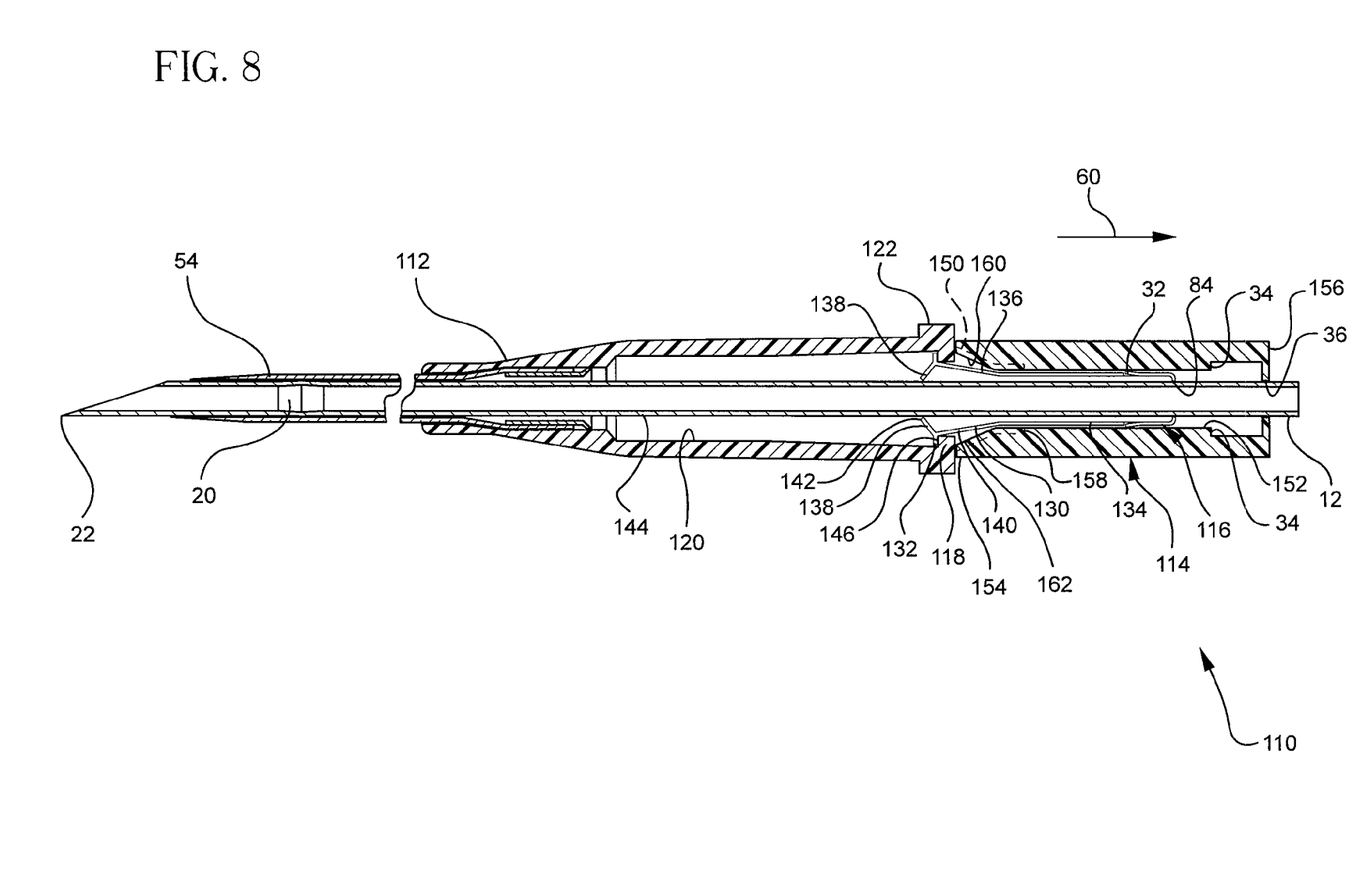
FIG. 8 is a cross-sectional view of a vascular access system, incorporating a safety clip, prior to insertion of the catheter into a patient.
Figure 9:
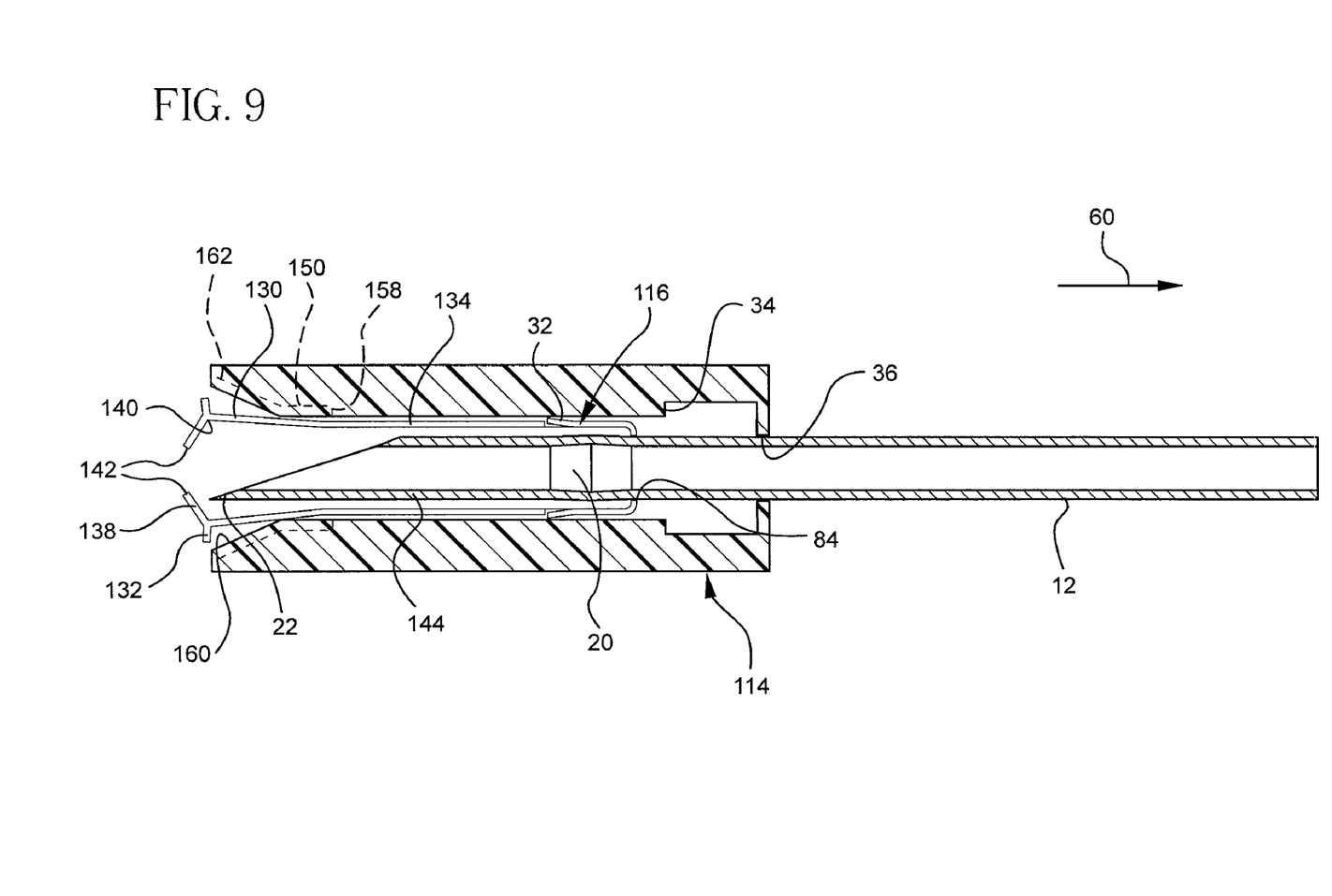
FIG. 9 is a cross-sectional view of a safety clip and needle being withdrawn into a sleeve member.
Figure 10:
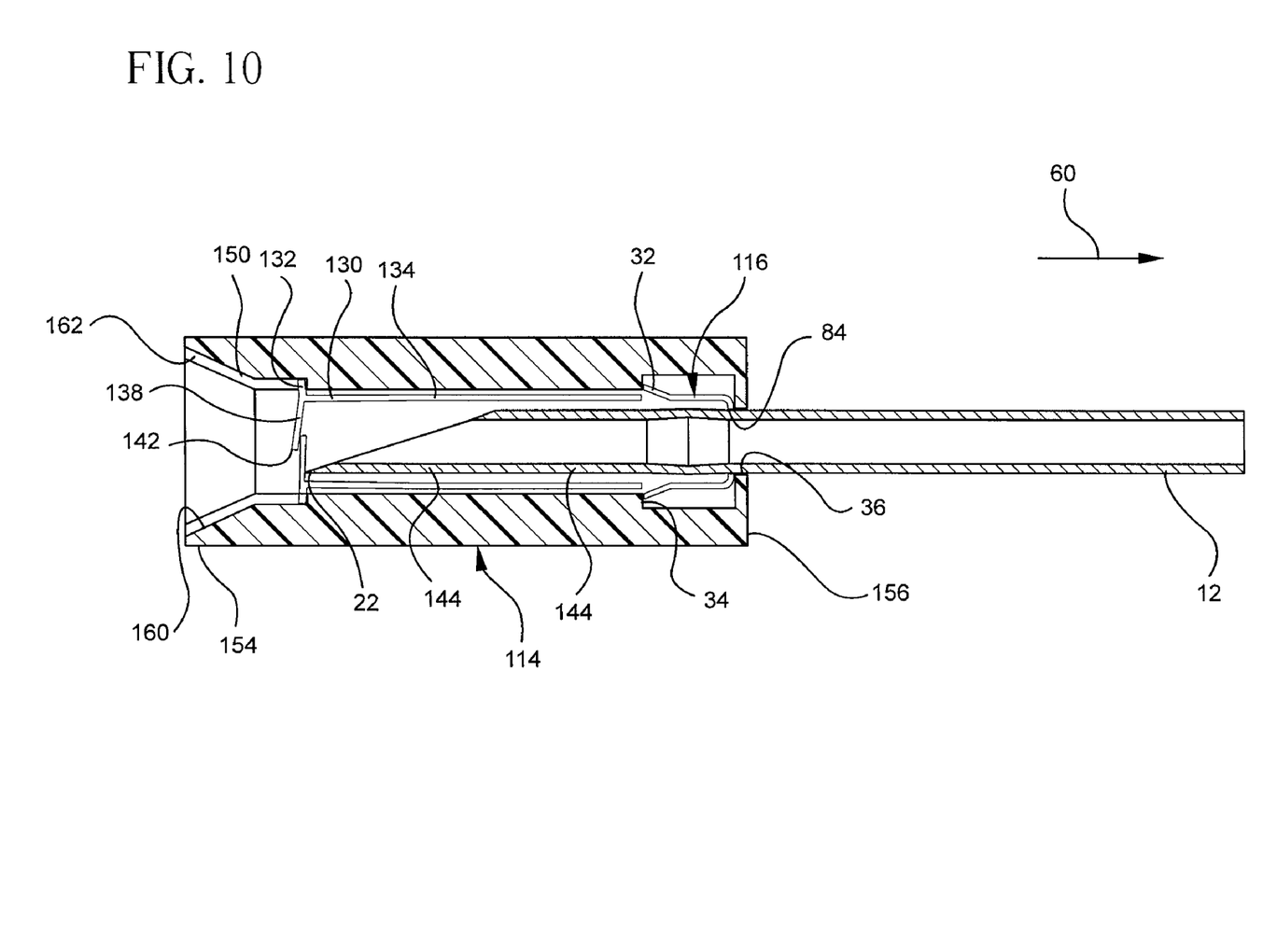
FIG. 10 is a cross-sectional view of a sleeve retaining a needle and safety clip following removal of the sleeve from the catheter adapter.

Referring now to FIGS. 8-10, an embodiment of the needle shielding assembly 110 is illustrated. The needle shielding assembly 110 includes a needle 12, a catheter adapter 112, a sleeve 114, and a safety clip 116. In this embodiment, the safety clip 116 is modified to include at least one arm 134 having an interlock flange 130 at the distal end of the arm 134. The interlock flange 130 includes a flap 138 extending inwardly from the distal end 140 of the interlock flange 130. As positioned, the free end 142 of the flap 138 pinches the shaft of the needle 12 to apply a slight pressure to the outer surface 144 of the needle 12. As such, the presence of the needle 12 outwardly biases the interlock flange 130. The interlock flange 130 further comprises an interlock finger 132 extending outward from the distal end 140 of the interlock flange 130. The interlock finger 132 is positioned in a direction generally opposite to the flap 138 such that the interlock finger 132 forms an interface 146 with the inner surface of the interlock ring 118. The flap 138 may be linear or contoured to provide effective shielding and retention of the needle tip 22 as well as retention of any residual fluids exuded from the needle tip 22 following use of the needle 12.

The catheter adapter 112 includes an interlock ring 118. The interlock ring 118 is positioned at the opening of the first end 122 of the catheter adapter 112 and comprises an inward, annular extension of the inner surface 120 of the catheter adapter 112. The depth and width of the interlock ring 118 is selected so as to provide a compatible surface for engaging the interlock finger 132 of the interlock flange 130. The interlock flange 130 is outwardly biased by the presence of the needle 12, such that the needle 12 is pinched by the free end 142 of the flap 138 resulting in an outward displacement of the interlock flange 130. As such, the interlock finger 132 engages the interlock ring 118 and forms an interface 146 between the interlock finger 132 and the interlock ring 118. Thus, the catheter adapter 112 and the sleeve 114 are supported and locked together by this interface.

The sleeve 114 is modified to include at least one interlock finger channel 150 formed on the inner surface 152 of the sleeve 114. The interlock finger channel 150 is a recessed groove formed on the inner surface 152 of sleeve 114. The interlock finger channel 150 extends from the distal end 154 of the sleeve 114 to the proximal end 156 of the sleeve 114, and terminates in an interlock finger catch 158. The interlock finger catch 158 is the terminal end of the interlock finger channel 150 and is located at a point prior to the proximal end 156 of the sleeve 114. The interlock finger channel 150 is designed to compatibly receive the interlock finger 132 of the safety clip 116. The interlock finger 132 translates within the interlock finger channel 150 from the distal end 154 of the sleeve 114 to the proximal end 156 of the sleeve 114. At one point, the interlock finger 132 engages the interlock finger catch 158 and the safety clip 116 is prevented from further retraction into the sleeve 114. The location of the interlock finger catch 158 is selected so as to coordinate the simultaneous interaction of the interlock finger 132 with the interlock finger catch 158, and the barb 32 with the barb catch 34. As such, when the safety clip 116 is drawn towards the proximal end 156 of the sleeve 114, both interactions occur simultaneously and the safety clip 116 is locked in place within the sleeve 114.

The sleeve 114 is further modified to minimize the tolerance between the inner surface 152 of the sleeve 114 and the barb 32 of the safety clip 116. As such, the barb 32 maintains contact with the inner surface 152 of the sleeve 114. The interaction of the barb 32 and the inner surface 152 of the sleeve 114 prevents the safety clip 116 from translating towards, or exiting, the distal end 154 of the sleeve 114. Therefore, the safety clip 116 is only able to translate towards, and exit through, the proximal end 156 of the sleeve 114. The one-way movement of the safety clip 116 further secures the locked position of the sleeve 114 and the catheter adapter 112, and prevents any disruption of the interface 146.

The interlock finger channel 150 and engaged interlock finger 132 may also provide radial alignment of the safety clip 116 within the sleeve 114. The distal end 154 of the sleeve 114 is further modified to provide a tapered opening 160. The tapered opening 160 provides clearance for the outwardly biased interlock flanges 130. Therefore, the interlock flanges 130 may be outwardly biased without contacting or pivoting on the inner surface 152 of the sleeve 114.

The needle shielding assembly 110 is actuated following insertion of the catheter 54 into the patient. Following catheterization, the needle 12 is removed from the catheter 54 in a proximal direction 60. As the needle 12 is removed, the needle feature 20 passes under the first and second flaps 138. The first and second interlock flanges 130 are further biased outwardly to by the passage of the needle feature 20. As the needle 12 continues in the proximal direction 60, the needle tip 22 is drawn past the first and second flaps 138. At this point, the first and second interlock flanges 130 relax inwardly, shielding the needle tip 22. Additionally, the inwardly relaxed interlock flanges 130 release the first and second interlock fingers 132 from the interlock ring 118. As such, interlock fingers 132 become disengaged from the interlock ring 118, and the sleeve 114 and the catheter adapter 112 are no longer connected together.

At this point, the needle feature 20 abuts the cannula port 84 of the safety clip 116. As such, the larger diameter needle feature 20 is prevented from translating in a proximal direction 60 beyond the smaller diameter cannula port 84. Therefore, as the needle 12 is drawn in a proximal direction 60, the needle feature 20 binds on the cannula port 84, causing the safety clip 116 to translate with the needle 12 in a proximal direction 60.

As the needle 12 and the safety clip 116 translate in a proximal direction 60, the interlock fingers 132 engage the interlock channels 150. At this point, the interlock fingers 132 translate within the interlock channels 150 in a proximal direction 60. The interlock fingers 132 continue to translate through the interlock channels 150 until the interlock fingers 132 contact the interlock finger catch 158. At this point the safety clip 116 and enclosed needle 12 are prevented from further movement in the proximal direction 60. As the interlock fingers 132 travel through the interlock channels 150, the tapered opening 160 of the sleeve 114 inwardly bias the flaps 138. As such, the flaps 138 are brought into a position such that the flaps 138 overlap one another and are closed in front of the needle tip 22. In this position, the flaps 138 shield the needle tip 22 and further enclose the needle tip 22 within the safety clip 116.

With the flaps 138 closed and shielding the needle tip 22, the safety clip 116 continues to translate in a proximal direction 60 until the interlock fingers 132 initiate contact with the interlock finger catch 158 of the interlock channels 150. Simultaneous with this contact, the barbs 32 engage their respective barb catch 34 thereby locking the safety clip 116, and the enclosed needle tip 22, within the lumen of the sleeve 114.

Various modifications to the needle shield assemblies of the present invention are possible while staying within the same inventive concept. For example, the needle shield assemblies can be used to protect the tip of a cannula in an IV catheter, a stylet in a long anesthesia needle, a catheter adapter, and other such medical devices. The cross section of the needle shield assembly and/or tubular housing can be of other shapes such as square, rectangular, triangular, oval, polygonal, and the like. The feature of the needle can be non-symmetrical and formed other than by crimping the shaft or affixing a ferrule. Any structure may be used to provide an interlock and interlock mate. The needle shield may include one or more blood stabilizing materials to further limit the risk of blood exposure. The blood stabilizing material may be disposed on one or more internal or external surfaces of the sleeve, the safety clip and/or needle shield assembly. Additionally or alternatively, the blood stabilizing material may be incorporated as a solid or semi-solid ring having a passage through which the needle closely passes. The blood stabilizing material may be a coagulant, an absorbent, or another material for stabilizing the blood to reduce the exposure risk. Similarly, the blood stabilizing material may be a liquid, a solid, a gel, a powder, granular, or any other consistency appropriate for its use. The blood stabilizing material may be disposed in a porous membrane or container that allows the blood to enter while preventing the exit of the blood stabilizing material. Further, any element of any embodiment described above may be combined in any number or orientation with any other element of any embodiment.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A device for shielding a needle tip, comprising:
a sleeve interlocked with a catheter adapter;
a safety clip partially housed within the sleeve, and partially housed within the catheter adapter, a portion of the safety clip outwardly biasing an interlock flange of the sleeve into an interlock mate of the catheter adapter; and
a needle extending through the sleeve, the catheter adapter, and the safety clip;
wherein upon removal of the needle from the proximal end of the catheter adapter, the tip of the needle is retained within the safety clip and prevented from reemerging from the safety clip, and the safety clip is retained within the sleeve.

2. The device of claim 1, wherein the sleeve and the catheter adapter are disengaged from one another by removing the safety clip from the catheter adapter.

3. The device of claim 2, wherein the tip of the needle is retained within the safety clip prior to the safety clip being removed from the catheter adapter.

4. The device of claim 3, wherein the tip of the needle is retained within the safety clip prior to the safety clip being entirely withdrawn into the sleeve.

5. The device of claim 4, wherein the interlock flange of the sleeve is relaxed inwardly to disengage from the interlock mate, and to retain the safety clip within the sleeve.

6. The device of claim 5, wherein a barb of the safety clip interacts with a barb catch of the sleeve to further retain the safety clip within the sleeve.

7. A method for retaining a needle tip, comprising:
interlocking a sleeve and a catheter adapter;
housing a safety clip partially within the sleeve and partially within the catheter adapter; and
extending a needle through the sleeve, the catheter adapter, and the safety clip;
wherein upon removal of the needle from the proximal end of the catheter adapter, the tip of the needle is retained within the safety clip and prevented from reemerging from the safety clip, and the safety clip is retained within the sleeve;
wherein the sleeve and the catheter adapter are disengaged from one another by removing the safety clip from the catheter adapter.

8. The method of claim 7, wherein a portion of the safety clip outwardly biases an interlock flange of the sleeve into an interlock mate of the catheter adapter.

9. The method of claim 7, wherein the tip of the needle is retained within the safety clip prior to the safety clip being removed from the catheter adapter.

10. The method of claim 9, wherein the tip of the needle is retained within the safety clip prior to the safety clip being entirely withdrawn into the sleeve.

11. The method of claim 10, wherein the interlock flange of the sleeve is relaxed inwardly to disengage from the interlock mate, and to retain the safety clip within the sleeve.

12. The method of claim 11, wherein a barb of the safety clip interacts with a barb catch of the sleeve to further retain the safety clip within the sleeve.

13. An apparatus for shielding a needle tip following catheterization of a patient comprising:
- a sleeve interlocked with a catheter adapter, the sleeve comprising at least one interlock flange compatibly engaged within the at least one interlock mate of the catheter adapter;
- a safety clip partially disposed within the sleeve and partially disposed within the catheter adapter, the safety clip having a set of opposing arms that pinch a portion of the needle; and
- a needle extending through the sleeve, the catheter adapter, and the safety clip;
- wherein upon removal of the needle from the proximal end of the catheter adapter, the tip of the needle is retained within the safety clip and prevented from reemerging from the safety clip, and the safety clip is retained within the sleeve.

14. The apparatus of claim 13, wherein the set of opposing arms outwardly bias the at least one interlock flange into the at least one interlock mate.

15. The apparatus of claim 14, wherein upon withdrawal of the needle from the catheter adapter, the set of opposing arms no longer pinches the portion of the needle thereby releasing the outwardly biased interlock flange from the engaged interlock mate.

16. The apparatus of claim 15, wherein the sleeve further comprises a lumen for receiving the safety clip and the retained needle tip.

17. The apparatus of claim 16, wherein the sleeve further comprises at least one clip catch mate for irreversibly engaging at least one clip catch of the safety clip, thereby locking the safety clip within the lumen of the sleeve.

* * * * *